United States Patent [19]

Delmotte et al.

[11] Patent Number: 4,753,984

[45] Date of Patent: Jun. 28, 1988

[54] WATER SOLUBLE MACROMOLECULAR PRODRUGS, THEIR PREPARATION AND THEIR USE AS ANTITUMOR AND ANTIPARASITE MEDICINES

[75] Inventors: Francis Delmotte, Olivet; Michel Monsigny, Saint-Cyr-en-val; Pierre-Jean Lescanne, Etampes; Francois Daussin, Saint-Jean-le-Blanc, all of France

[73] Assignee: Centre National de la Recherche Scientifique (CNRS), Paris, France

[21] Appl. No.: 871,883

[22] Filed: Jun. 9, 1986

[30] Foreign Application Priority Data

Jun. 7, 1985 [FR] France .................................. 85 08648

[51] Int. Cl.$^4$ ...................... A61K 37/20; A61K 9/00; A61K 31/765
[52] U.S. Cl. ...................................... 525/54.1; 514/2; 530/300
[58] Field of Search ............................ 525/54.1, 54.11; 530/333, 334, 300; 514/2, 21; 526/238.1

[56] References Cited

U.S. PATENT DOCUMENTS 4,479,932 10/1984 Bodor ................................... 546/316
4,638,045 1/1987 Kohn et al. .......................... 528/328

FOREIGN PATENT DOCUMENTS 0037388 10/1981 European Pat. Off. .
1541436 2/1979 United Kingdom .

OTHER PUBLICATIONS

Advances on Polymer Science, vol. 57, 1984, pp. 51–101, Springer Verlag, Berlin, DE: K. Dusek et al; "Polymers in Medicine".

Primary Examiner—Delbert R. Phillips
Assistant Examiner—Nathan M. Nutter
Attorney, Agent, or Firm—Cushman, Darby & Cushman

[57] ABSTRACT

A prodrug comprises a polyhydroxylated polyamine to which a drug is linked by the intermediary of a peptidyl group. The prodrug is useful as an antitumor or antiparasite medicine.

9 Claims, 5 Drawing Sheets

Fig. 2.

Plasmatic Elimination of the Polymer of Example 2 labelled at $^{14}C$
— • — : intravenous injection ($4 \times 10^5$ c.p.m.)
— o — : intraperitoneal injection ($4 \times 10^5$ c.p.m.)
c.p.m. : strokes per minute

Fig. 3.

Localization of the (14-$^{14}$C) Daunorubicin either free or in the form of the polymer of Example 2 in C 57 B1/6 mice carriers of a Lewis pulmonary carcinoma

Fig. 4.

↓ : Measurement of the tumoral growth as a function of time
  days of injection of various products, o: physiologic serum
▲ : free Daunorubicin (100 micrograms/injection), o: Polymer
  of Example 2 (200 micrograms/injection in equivalents of
  Daunorubicin).

Fig. 5.

Measurement of the survival of treated animals; Jo: intramuscular implantation of $10^5 3$ LL cells, ↓: days of injection of various products, o--o--o: physiologic serum, ▲--▲--▲: Free Daunorubicin (100 micrograms injection, ●--●--●: Polymer of Example 2 (200 micrograms/injection in equivalents of Daunorubicin).

WATER SOLUBLE MACROMOLECULAR PRODRUGS, THEIR PREPARATION AND THEIR USE AS ANTITUMOR AND ANTIPARASITE MEDICINES

The present invention relates to new water soluble, macromolecular prodrugs, to their preparation and to their use as medicines.

It is known that prodrugs can be produced which impart principally a delay effect or which facilitate the transfer of the drug in vivo. These known prodrugs are prepared by linking the drug, that is the active principle, to a peptide. However, because of the low water solubility of these known prodrugs they exhibit certain disadvantages in their preparation as well as their efficacy.

The present invention relates to new prodrugs comprising essentially a drug or active substance linked by a covalent bond to a polyhydroxylated polymer by the intermediary of a peptidyl group, the said polyhydroxylated polymer being a polymer having at least 20% of units which are polyhydroxylated units and in particular those characterized by the fact that the ratio of the average number of molecules of active substance fixed on a molecule of the polymer to the average number of hydroxy groups present in a molecule of the polymer can range from about $10^{-2}$ to $10^{-4}$.

In other words, the macromolecular prodrugs of the present invention have the formula wherein
M is the residue of a polymeric molecule wherein at least 20% of its units are polyhydroxylated units,
P is a peptidyl group,
D is the residue of the drug molecule and
n represents the number of drug molecules fixed on the polymeric molecule, M.

Preferably, the drug is an amino drug linked to the peptidic group P by its C-terminal extremity, and in this case the peptide P is linked to the polymeric molecule M by the intermediate of a covalent bond (for example an amide bond); this covalent bond arising from the reaction of the N-terminal extermity of the peptide with a reactive group (for example a carboxylic group) carried by the polymeric molecule (corresponding to M) used in the preparation of the prodrug.

Representative compounds of Formula I include in particular:

(A) Those for which M represents the residue of an acrylamide substituted at the nitrogen by a polyhydroxylated hydrocarbon group.

Representative polymers of this type include principally those which are described in French Pat. No. 77,23223 (publication No. 2.398.762);

(B) Those for which M is the residue of a homopolymer of a diamino amino acid whose amine group which is not involved in the polymeric bonding is substituted by a polyhydroxyalkanoyl group;

Representative derivatives of this type include, in particular, polymeric molecules based on polylysine whose $-NH_2$ groups which are not involved in the polymeric bonding are acylated by an acylation agent derived from a polyhydroxy alkanoic acid; and (C) Those for which M is the residue of a homopolymer of an amino dicarboxylic acid of which a part of the carboxylic acid groups which are not involved in the polymeric bond are amidified by a polyhydroxy alkylamine wherein the amine is a primary or secondary amine.

In this case, the remaining carboxylic groups of the molecule corresponding to M establish covalent bonds with the $-(P-D)$ groups indicated in Formula I. Representative derivatives of this type, include in particular derivatives of polyglutamic acid or polyaspartic acid.

In other words, the polymers of Formula I are in particular:

(a) polymers I A comprising essentially units of the formula wherein
$R_1$ and $R_2$ represent $-H$ or lower alkyl,
$X^1$ represents $-CO-NH-R^3$,
$X^2$ represents $-CO-NH-X-CO-P-D$,
$R^3$ represents a polyhydroxylated hydrocarbon,
X represents a hydrocarbon group having 1-8 carbon atoms, optionally interrupted by 1 or more oxygen, sulfur or nitrogen heteroatoms, and
P and D have the meanings given above;

(b) polymers 1 B comprising essentially units of the formulas wherein
$X^3$ represents $-(CH_2)_x-NH-CO-R^4$,
$X^4$ represents $-(CH_2)_x-NH-CO-P-D$,
x is a number ranging from 1 to 4,
$R^4$ is a polyhydroxylated hydrocarbon, and
P and D have the meaning given above; and (c) polymers 1 C comprising essentially units having the formulas wherein
$X^5$ represents $-(CH_2)_y-CO-NH-R^5$,
$X^6$ represents $-(CH_2)_y-CO-P-D$,
y is a whole number ranging from 1 to 4,
$R^5$ is a polyhydroxylated hydrocarbon, and
P and D have the meanings given above.

However, the present invention also extends to the use of copolymers containing, in addition to the units mentioned above, units derived from co-monomers which can vary, in a known manner, the properties of the polymer. As indicated earlier, polymers I A, I B and I C contain, respectively, at least 20% of units II A, II B and II C.

Generally, the molecular mass, determined for example by the light diffusion method of the polymer corresponding to M, is greater than 5,000. It is for example between 10,000 and 500,000.

Representative peptides represented by P, include, in particular, those which include a peptidic sequence hydrolyzable by a specific protease, in particular, a protease secreted by the target cells of the active drug, for example, by tumoral cells, by a pathogenic microorganism, or by cells associated with a tumor, or again after endocytase, by the protease of lysosomes. The interest in using such peptidic sequences is that, in this case, the active drug is liberated only in the environment of the target or, often endocytase, at the very interior of the target cells, which thereby improves the efficacy of the drug.

In a general manner, the peptidic sequences represented by P must be considered as known.

Representative derivatives of Formula I, include, in particular, those for which the —P—D groups are those which carry sequences listed below (without that this list being limiting), it being understood that the sequences indicated are the minimal sequences and that it is possible to insert 1 to 3 other amino acids between the molecule M and the peptidic sequence indicated:

-L-Ala-L-Ala-L-Pro-L-Ala-D,
-L-Ala-L-Ala-L-Pro-L-Ala-L-Leu-D,
-L-Ala-L-Ala-L-Pro-L-Ala-D,
-L-Ala-L-Ala-L-Pro-L-Ala-L-Leu-D,
-L-Ala-L-Ala-L-Pro-L-Val-D,
-L-Ala-L-Ala-L-Pro-L-Val-L-Leu-D,
-L-Ala-L-Ala-L-Pro-L-Val-D,
-L-Ala-L-Ala-L-Pro-L-Val-L-Leu-D,
-L-Phe-L-Val-L-Arg-D,
-L-Phe-L-Val-L-Arg-L-Leu-D,
-L-Phe-L-Val-L-Arg-D,
-L-Phe-L-Val-L-Arg-L-Leu-D,
-L-Phe-L-Ala-L-Lys-D,
-L-Phe-L-Ala-L-Lys-L-Leu-D,
-L-Phe-L-Ala-L-Lys-D,
-L-Phe-L-Ala-L-Lys-L-Leu-D,
-Gly-Gly-L-Arg-D,
-Gly-Gly-L-Arg-L-Leu-D,
-Gly-Gly-L-Arg-D,
-Gly-Gly-L-Arg-L-Leu-D,
-Gly-Gly-L-Tyr-D,
-Gly-Gly-L-Tyr-L-Leu-D,
-Gly-Gly-L-Tyr-D,
-Gly-L-Phe-L-Ala-L-Leu-D,
-Gly-L-Pro-L-Arg-L-Leu-D,
-L-Pro-L-Phe-L-Arg-D,
-L-Pro-L-Phe-L-Arg-L-Leu-D,
-L-Pro-L-Phe-L-Arg-D,
-L-Pro-L-Phe-L-Arg-L-Leu-D and
-L-Val-L-Leu-Gly-L-Arg-D.

The drug D is for example daunorubicin, adriamycin and puromycin, which are antitumor drugs; and primaquine and chloroquine which are antiparasite drugs, etc.

The invention also relates to the use, in the production of a prodrug, of a polyhydroxylated polymer such as defined above, to which the drug is joined by the intermediate of a peptidyl group.

The polymer and the peptidyl arm are principally those which are defined above.

The invention also relates to a process for preparing the macromolecular prodrugs defined above.

This process comprises principally:

(a) either untilizing as the initial reactant a macromolecule containing polyhydroxylated units that are etherified with a hydrocarbon group containing a protected carboxylic group, submitting the resulting ether to a deprotection reaction of the carboxyl groups and reacting the resulting compound with a peptidyl-drug compound such as one having the formula, H—P—D wherein P and D are defined above, or (b) utilizing as the initial reactant a polycarboxylated macromolecule whose carboxylic group is activated and reacting the said active carboxylic groups, partially with a peptidyl-drug compound such as one having the formula H-P-D, P being defined as above, and partially with a primary or secondary polyhydroxylated amine such as one having the formula, $R_5$-$NH_2$, wherein $R_5$ is defined;

or (c) utilizing as the initial reactant a polyaminated macromolecule that is reacted with an acylation agent derived from a polyhydroxylated carboxylic acid to obtain, by an amidification reaction, a polyhydroxylated molecule which is subjected to the synthesis procedures set forth in (a) above.

In these particular embodiments, the process of the invention can exhibit the following characteristics, singly or in combination:

Process (a)

The polyhydroxylated macromolecule is etherified to form an alkaline alcoholate which is then reacted with a halogenated derivative of a hydrocarbon group carrying a protected carboxylic group;

The carboxylic group is protected, for example, in the form of an ester, in particular, a lower alkyl ester and, in this case, the carboxylic group is deprotected by saponification;

The deprotected carboxylic groups react with the peptidic derivative, H—P—D, in the presence of an activation agent; the activation agent is for example a carbodiimide such as dicyclohexyl carbodiimide in the presence of hydroxybenzotriazole or any other known activation agent in peptidic synthesis.

Process (b)

The carboxylic group of the polycarboxylated macromolecule is activated under conditions analogous to those employed in process (a).

Process (c)

The acylation agent which is reacted with the polyamino macromolecule is, for example, a lactone such as glucono-deltalactone, ribono-lactone, the lactone of heptaglyconoic or octaglyconoic acids, etc.

The products of the formula, H—P—D are obtained by coupling the peptidic sequence P, protected at the N-terminal side in accordance with known procedures (for example by formation of the N-trityl derivative) with the drug D having an amino function, in the presence of an activation agent such as for example hydroxybenzotriazole, then deprotecting the N-terminal group. The conditions of deprotection of the coupling product must obviously be compatible with the stability of the drug.

The starting peptides, corresponding to sequence P in Formula I and commercially available or they can be synthesized in accordance with known methods of peptide synthesis (see for example E. Cross and J. Meienhoffer, 1979, "The peptides: Analysis, synthesis, biology", Academic Press, New York, Volumes I, II, III and following).

The invention also relates to pharmaceutical compositions comprising as the active component, at least one prodrug I, I A, I B or I C, such as defined above, optionally in combination with an appropriate excipient.

The invention also relates to the use of the prodrugs such as defined above in the industrial manufacture of medicines.

The prodrugs of the present invention are used as medicines in dosages corresponding to conventional dosages of the active drug that they include, or even at higher dosages, since experience has shown that these prodrugs have a toxicity lower than that of an equivalent amount of the drug they include.

The prodrugs of the present invention have, however, the same therapeutic properties as the drugs they include.

The drugs present in the prodrugs of this invention are principally antitumor agents, antibacterial or antiparasite agents.

When these drugs are antitumor agents, the medicines of the invention are employed principally as agents to inhibit the proliferation of tumors or as agents to prevent metastasis formation. The effective dosage varies generally from 1 to 20 mg of active principle/kg of body weight.

When the drugs present in the medicines of this invention are antiparasite agents, the medicines are employed principally as agents in the treatment or prevention in the field of combatting parasites responsible for various illnesses called "tropicals".

The medicines of the present invention are administered by any convenient method. It is necessary to note, however, that oral administration is generally not convenient.

The medicine can be provided principally in the form of injectable solutions, lyophilized powders to be diluted in a physiologic serum, solutions or emulsions for application to the skin or mucous membrane or solutions packaged under pressure as aerosols, and the like.

The following non-limiting Examples illustrate the present invention.

EXAMPLE 1

Preparation of a polycarboxylated linear polymer of 2-N-acryloylamino-2-hydroxymethyl-1,3-propanediol substituted by the -Gly-Gly-L-Tyr-Daunorubicin sequence

Stage 1

To a linear polymer of 2-N-acryloylamino-2-hydroxymethyl-1,3-propanediol having a molecular mass of 200,000 (1 g; 5 micromoles) obtained in accordance with the process disclosed in French Pat. No. 77.23223 (2.398.762) in solution in anhydrous N,N-dimethyl-formamide (20 ml), there is added sodium hydride (0.8 mmoles). After stirring for 12 hours at ambient temperature, there is added to the viscous solution the polyalcoholate of methylbromoacetate (0.4 mmoles). The reaction is maintained with stirring for 4 hours at ambient temperature. The reaction mixture is then neutralized with a resin sold under the trade name Dowex AG-50 W X 8 (4 ml), then dialyzed against water. The aqueous solution is then lyophilized (0.98 g). The methyl-ester functions thus introduced are characterized in IR by a vibration band at 1740 cm$^{-1}$.

Stage 2

The polymer obtained in Stage 1 is saponified by soda and after neutralization by a resin sold under the trade name Dowex AG-50 X W 8, a polymer substituted by 75 carboxyl groups with a yield of 81% after lyophilization is obtained.

Stage 3

The polymer obtained in Stage 2 (400 mg, or essentially 2 micromoles) is dissolved in N,N-dimethylformamide (2 ml) in the presence of Gly-Gly-L-Tyr-Daunorubicin.HCl (34 mg, 40 micromoles) and triethylamine (28 microliters, or 200 micromoles). After the addition of hydroxybenzotriazole (7.7 mg, 50 micromoles) and dicyclohexyl carbodiimide (10.3 mg, 50 micromoles), the reaction mixture is stirred for 48 hours at ambient temperature out of contact with light. At this stage, the residual carboxylic functions are modified to an amide form by the addition of tris (hydroxymethyl) aminoethane (24 mg, 200 micromoles) in the presence of hydroxybenzotriazole (30.6 mg) and dicyclohexyl carbodiimide (41.2 mg). After dilution, dialysis against water and centrifuging the insoluble residue, the polymer is lyophilized (392 mg). The measure of absorption at 495 nm confirms that a molecule of polymer contains on average 15 residues of Gly-Gly-L-Tyr-Daunorubicin. The fixation yield is 73%.

EXAMPLE 2

Preparation of a polycarboxylated linear polymer of 2-N-acryloylamino-2-hydroxymethyl-1,3-propanediol substituted by the -Gly-Gly-L-Tyr-L-Leu-Daunorubicin sequence The polymer obtained in Stage 2 of Example 1 is coupled, under the conditions employed in Stage 3 of Example 1, to the sequence -Gly-Gly-L-Tyr-L-Leu-Daunorubicin, except using 18 equivalents of this derivative due to the hydrophobic character of the peptidic sequence. Thus, 13 residues of peptidyl Daunorubicin have been fixed per molecule of polymer with a yield of 69%.

In a similar manner, the same polymer, except that it is $^{14}$C labelled on the daunorubicin in position 14 is prepared.

EXAMPLE 3

Preparation of a polycarboxylated linear polymer of 2-N-acryloylamino-2-hydroxymethyl-1,3-propanediol substituted by the Gly-L-Phe-L-Ala-L-Leu-Daunorubicin sequence The procedures described in Example 1, Stage 3, are repeated except that 16 equivalents of the compound Gly-L-Phe-L-Ala-L-Leu-Daunorubicin are used in the reaction. Under these conditions, 11 residues of peptidyl-Daunorubicin are coupled per molecule of polymer for a yield of 70%.

EXAMPLE 4

Preparation of a polycarboxylated linear polymer of polygluconoyl polylysine substituted by the Gly-Gly-L-Tyr-L-Leu-Daunorubicin sequence

Stage 1

Commercial poly-L-lysine (manufactured by BACHEM-500 mg) having an average molecular mass of 50,000 is dissolved in 20 ml of a 3:1 N,N-dimethylformamide/dimethylsulfoxide solvent system, then deprotonated by the addition of triethylamine (335 microliters). This solution is brought to 50° C. and every 6 hours glucono-delta-lactone is added for a period of 24 hours (4 times 425 mg). After cooling, the reaction mixture is diluted with water (40 ml), dialyzed, then lyophilized (470 mg). After dosage, the modified poly-L-lysine no longer has free amine functions.

Stage 2

The polygluconoyl polylysine polymer prepared above is modified according to the protocol described in Stages 1 and 2 of Example 1, thus providing a polymer substituted by 20 carboxylic groups.

Stage 3

The polymer obtained in Stage 2 of this Example (470 mg, 9 micromoles) is solubilized in N,N-dimethylformamide in the presence of Gly-Gly-L-Tyr-L-Daunorubicin (86 mg, 90 micromoles) and triethylamine (28 microliter, or essentially 200 micromoles). After the addition of hydroxybenzotirazole (14.4 mg, 0.1 millimole) and dicyclohexylcarbodiimide (20.6 mg, 0.1 millimole), the reaction mixture is stirred for 48 hours at ambient temperature out of contact with light. The residual carboxylic functions are substituted in amide form by the addition of tris (hydroxymethyl) aminoethane. After dilution and dialysis against water, the polymer is lyophilized (460 mg). By measurement of the absorption at 495 nm, 9 residues of Gly-Gly-L-Tyr-L-Leu-Daunorubicin per molecule of polymer are calculated. The fixation yield is 75%.

EXAMPLE 5

Preparation of a polyhydroxylated poly-L-glutamate conjugated with the Gly-Gly-L-Tyr-L-Leu-Daunorubicin sequence

Stage 1

Commercial poly-L-glutamic acid (manufactured by BACHEM, 500 mg, $10^{-2}$ moles) having an average molecular mass of 50,000 is dissolved in anhydrous N,N-dimethylformamide (40 ml) in the presence of triethylamine (550 microliters, 3.9 moles) and Gly-Gly-L-Tyr-L-Leu-Daunorubicin (86 mg, 90 micromoles). After the addition of hydroxybenzotriazole (14.4 mg, 0.1 mmole) and dicyclohexyl carbodiimide (20.6 mg, 0.1 mmole) the reaction mixture is stirred for 48 hours at ambient temperature out of contact with light. The reaction mixture is diluted in a phosphate buffer. After one hour at 4° C., the insoluble material is removed by centrifugation, then dialyzed against water and finally lyophilized. On measurement of the absorption at 495 nm, 8 molecules of Gly-Gly-L-Tyr-L-Leu-Daunorubicin per molecule of polymer are noted.

Stage 2

The polymer isolated in Stage 1 (300 mg, 5.2 micromoles) is taken up in N,N-dimethylformamide (30 ml) in the presence of tris (hydroxymethyl)-aminoethane (242 mg, 2 mmoles). After the addition of hydroxybenzotriazole (283 mg, 2.1 mmole) and dicyclohexyl carbodiimide (432 mg, 2.1 mmols) the reaction mixture is stirred for 48 hours at ambient temperature. The polymer thus subsituted is dialyzed against water. The solid residue is removed by centrifugation and the supernatant is lyophilized.

By operating in this manner, all the carboxylic functions present on the polymer are quantitatively modified into the amide form of tris (hydroxymethyl) aminomethane. The absence of carboxylic functions is shown by pH-metric dosage.

Stage 3

The polymer isolated in Stage 1 (200 mg, 3.5 micromoles) is taken up in N,N-dimethylformamide (7 ml) in the presence of N-methylglucamine (45 mg, 2.3 mmoles). After the addition of hydroxybenzotriazole (356 mg, 2.3 mmoles) and dicyclohexyl carbodiimide (479 mg, 2.3 mmoles), the reaction mixture is stirred for one hour at 0° C., then for 16 hours at ambient temperature. The polymer thus substituted is isolated by precipitation and centrifugation in a 1:1 v/v N-butanol/ethyl acetate solvent system. It is then dialyzed several times against water for 48 hours. The insoluble residue is removed by centrifugation, and the supernatant is lyophilized.

Under these conditions, 85% of the carboxylic functions are modified into the amide form of N-methylglucamine.

Example 6

Preparation of a polycarboxylated linear polymer of 2-N-acryloylamino-2-hydroxymethyl-1,3-propanediol substituted by the Gly-L-Pro-L-Arg-L-Leu-Daunorubicin sequence.

The procedures as described in Example 1, Stage 3, are repeated, except that 20 equivalents of the compound Gly-L-Pro-L-Arg-L-Leu-Daunorubicin are used in the reaction. Under these conditions, 13 residues of the peptidyl-Daunorubicin are coupled per molecule of polymer with a yield of 65%.

EXAMPLE 7

Proteolyse in vitro

The chymotrypsic hydrolyse is effected in a Tris-HCl buffer 0.05 M, $CaCl_2$ 10 mM at pH=8.0.

On analysis, the derivatives of the daunorubicin are liberated after enzymatic hydrolysis, by thin layer chromatography. For example:

The polymer of Example 2 liberates leucyl-daunorubicin: Rf:0.4 in a 9:2 $CHCl_3/CH_3OH$ solvent system, the polymer of Example 1 frees the daunorubicin: Rf-0.56 in a 15:5:1:1 $CHCl_3/CH_3OH/H_2O$/acetic acid solvent system, the polymer of Example 3 frees alaninyl-leucyl-daunorubicin: Rf-0.32 in a 9:2 $CHCl_3/CH_3OH$ solvent system.

Trypsic hydrolysis is carried out in a 0.1M solution of sodium bicarbonate, $CaCl_2$, 10 mM at pH, 8.7.

The polymer of Example 6 is hydrolyzed by trypsin while freeing leucyl-daunorubicin: Rf-0.4 in a 9:2 $CHCl_3/CH_3OH$ solvent system.

Pharmacologic Properties (1) The cells of Lewis pulmonary carcinoma (3 LL) originating from a metastasis malignant tumor, develop spontaneously in C 57 BL/6 mice. J. C. Mayo (1972) Cancer Chem. Rep. Vol. 3, 325.

(a) Culture in vitro

These cells are cultivated in monolayers (sown at $2 \times 10^4$ cell/ml) in a MEM medium containing 20% of fetal calf serum at 37° C. and under a 5% $CO_2$-95% air atmosphere. At confluence (after 3 days) they are recovered by a short treatment (2 minutes) with a 0.02% EDTA solution in 0.1% PBS glucose. The cells are washed with a MEM medium, then taken up in a complete medium. Viability >95%.

(b) Solid tumor in vivo

The production of isolated cells starting with a solid tumor requires the use of proteases and chelating agents. The tumor is removed and freed of necrosed areas. It is then cut up into small fragments of about 1 $mm^3$ and suspended in PBS containing 0.1% glucose, for 10 minutes with stirring at 4° C. The supernatant is removed and the fragments are placed in the presence of trypsin (Trypsine Enzar T for cellular culture, Reheis Chemical Company, Armour Pharmaceutical, South Plainfield, U.S.A.), and 0.02% EDTA (Merck) in the glucosed PBS, at ambient temperature. The cells detach little by little and are collected, after 30 minutes in a centrifuge tube after filtration on a nylon sifting cloth (Monyl Ny 25 HC, 25 micrometer mesh, Polylabo, Strasbourg, France). After two washings in the glucosed PBS, the living cells are counted and the concentration adjusted.

(2) Cytotoxic activity in vitro

The cytotoxic activity is measured by inhibition of the incorporation of tritiated thymidine.

In the wells of a Limbro plate, there is introduced 1 ml of a cellular suspension of 3 LL cells at $10^4$ cells/ml in a MEM medium containing 20% of fetal calf serum. The cells are thus cultured for 24 hours. The culture medium is removed by aspiration and there is placed in each well, 1 ml of various dilutions of drug effected in the culture medium. The plates are placed in an oven for 43 hours. There are then added 20 microliters of a tritiated thymidine solution (0.5 microCurie, 18.5 KBq). After 4 hours of incubation the cells are separated with a safety scraper, then recovered on a glass fiber filter and washed. The radioactivity of the cells is measured in a beta scintillation counter after dissolution in a liquid scintillant.

The cytotoxic activity of the drugs and following conjugates has been determined on the 3 LL cells in accordance with the protocol described above:
free daunorubicine,
leucyl-daunorubicine,
Gly-Gly-L-Tyr-L-Leu-Daunorubicin,
Polymer of Example 1,
Polymer of Example 2 and
Polymer of Example 3.

Figure 1:
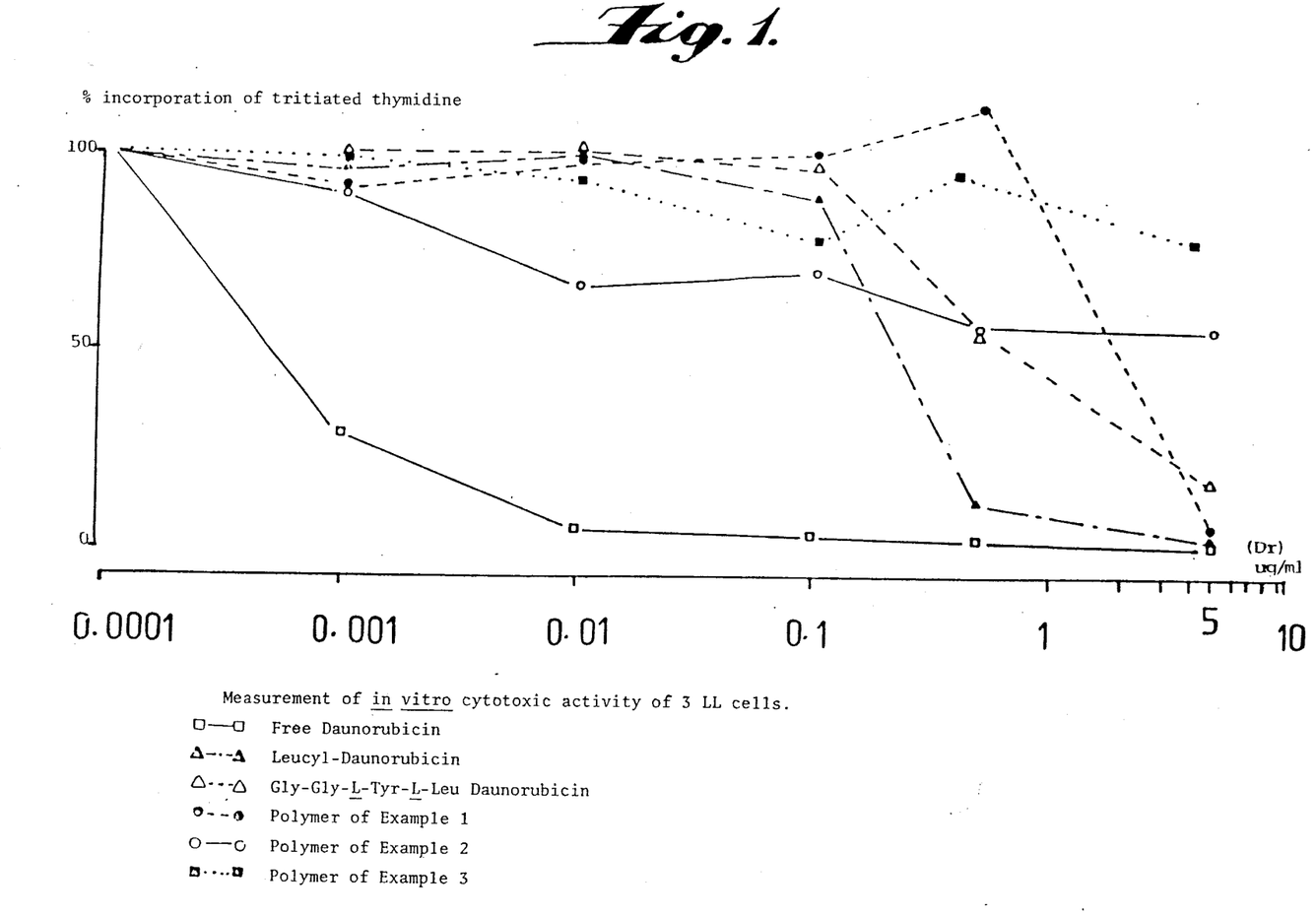

On the basis of the results obtained by incorporating $^3H$ thymidine combined in FIG. 1, it is seen that the substitution of Daunorubicin by a peptide, or better, its grafting onto the linear polymer, involves a more significant reduction of the cytotoxicity of this drug in vitro. The cytotoxic activity is modulated according to the peptidic sequence.

(3) Tests in vivo

In order to study the distribution of a macromolecular polymer in a mouse organism, after intravenous or intraperitoneal injection, and the duration of its plasmatic life, there is employed the polymer labelled with $^{14}C$ on Daunorubicin in position 14, prepared in Example 2.

(a) Plasmatic Clearance

The polymer labelled with $^{14}C$ in solution in physiologic serum at a concentration of 15 mg/ml is injected (200 microliters, 3 mg of polymer corresponding to 100 micrograms of Daunorubicin), either intravenously in a lateral vein of the tail, or by intraperitoneal injection.

The clearance of this polymer in the blood flow is measured by withdrawing 50 microliters of blood at various times after injection. The blood is removed from the plexus veins of the eye with the aid of a calibrated micropipette pretreated with an anticogulant. The activity present in each sample is counted after dilution in a liquid scintillant (2.5 ml).

Figure 2:
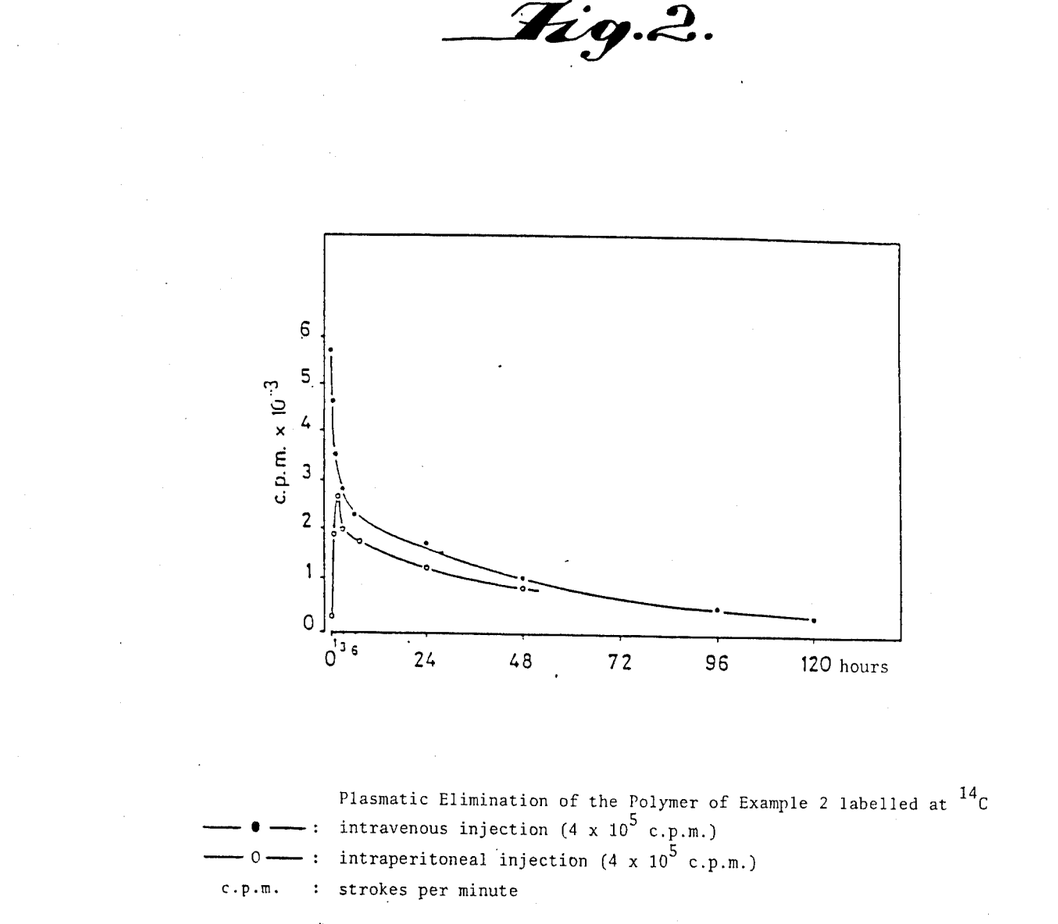

The results are shown in FIG. 2 and are recapitulated below:

The decrease of the plasmatic concentration of the polymer is relatively small. In effect, at the end of 48 hours 20% of the initial radioactivity is found. This is a quite remarkable result taking into account the fact that adriamycin disappears from plasma in 20 minutes.

Thin layer chromatographic analysis shows moreover that the radioactive material in the plasma is always present in macromolecular form. The tetrapeptide interposed between the polymer and the drug is then relatively resistant to seric proteases.

The macromolecular drug can pass through the peritoneal cavity in blood circulation. Three hours after injection, the plasmatic amount of the polymer injected intraperitoneally is similar to that of the polymer injected intravenously. Thin layer silica chromatography shows here again that the radioactive material in the plasma is also found in macromolecular form. But the repeated intraperitoneal injections can retard the transfer of the macromolecule from the peritoneal cavity toward the blood flow.

(b) Localization

The radiolabelled Daunorubicin drugs (14-$^{14}C$) are injected intravenously 14 days after implantation of $10^5$ 3 LL cells. Either 100 micrograms of free Daunorubicin ($5 \times 10^5$ cpm), or 100 micrograms of Daunorubicin in macromolecular form ($5 \times 10^5$ cpm) is injected. Localization is measured after the intravenous injection of various products.

The mice are sacrificed by cervical elongation 48 hours or 72 hours after injection. The organs are removed, dissolved by a tissue solubilizing agent (NCS Amersham) at a rate of 200 mg to 300 mg of organ/ml of solubilizing agent, then counted in a liquid scintillant. The tests have been carried out on lots of 3 mice with the polymer of Example 2 and free Daunorubicin. The results are recapitulated in FIG. 3.

Figure 3:
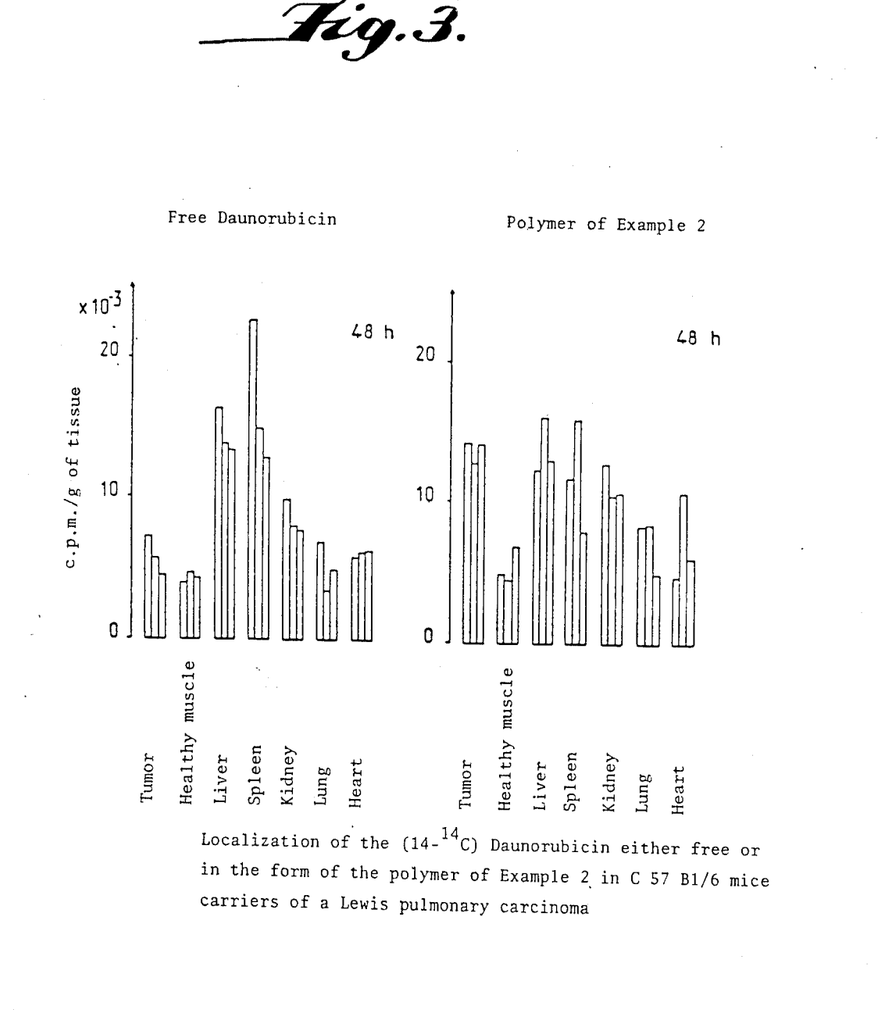

A general persistence of the Daunorubicin in the organism is observed when it is found in macromolecular form, principally at the tumor level.

Examination of the organs at the time of removal, then of their weight shows a severe atrophy of the spleen under the effect of the free Daunorubicin. This atrophy coincides with a significant accumulation of the radioactivity, whereas the spleens of the mice treated with the polymeric peptidyl drug have a weak radioactivity and a mass comparable to that of the healthy animals.

(c) Antitumor activity

The in vivo antitumor activity of the macromolecular drugs is evaluated on C 57 BL/6 male mice aged a total of about 10 weeks. $10^5$ 3 LL cells are implanted in each mouse by intramuscular injection of 100 microliters of a cellular suspension of $10^6$ cells/ml in the right posterior paw.

One lot of 10 mice, serving as a control, is injected with $7 \times 100$ microliters of physiologic serum.

One lot of 10 mice is treated with $7 \times 10$ micrograms of free Daunorubicin (dosage limited due to the toxicity of the free drug).

One lot of 10 mice is treated with the polymer of Example 2 at a rate of $8 \times 200$ microgram equivalents of Daunorubicin.

After intramuscular injection of the tumoral cells, the macromolecular prodrug is injected intravenously at days 2, 6 and 10, then intraperitoneally at days 14, 18, 22, 26 and 30.

Two parameters are recorded to evaluate the in vivo antitumoral activity: the inhibition of tumor growth and animal survival.

Figure 4:
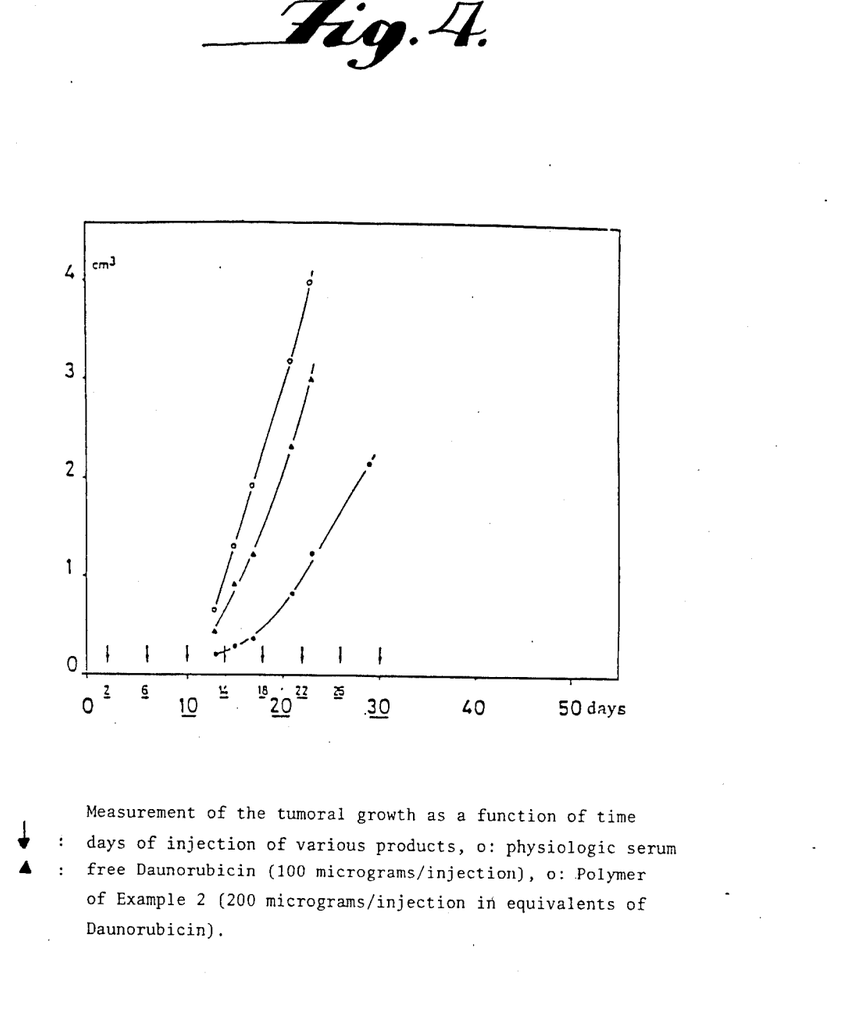

Examination of the tumor growth curve (FIG. 4) shows that the Daunorubicin even at the dosage employed (maximum dosage with regard to its toxicity) does not influence in a significant manner tumoral growth. The polymer of Example 2 on the other hand shows a significant inhibition of tumor growth at each point relative to the control lot.

Figure 5:
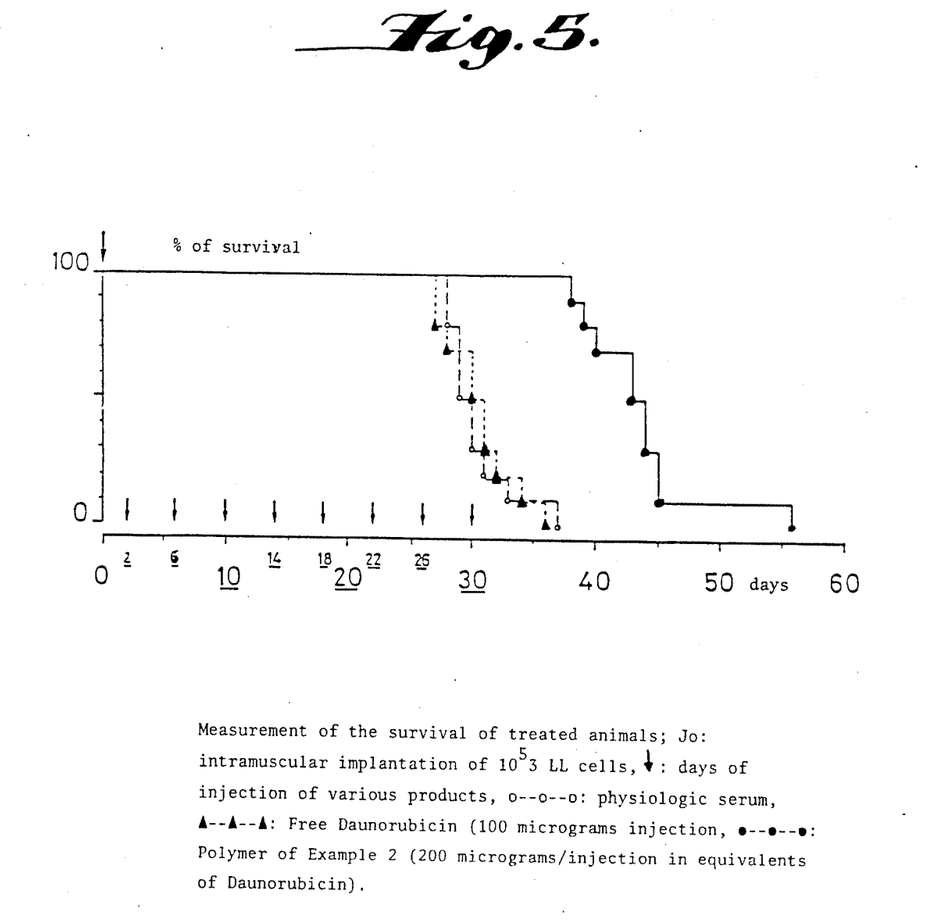

The second recorded parameter, survival of the animals treated relative to the control animals, confirms the antitumoral activity of the polymer of Example 2 (FIG. 5). The T/C measured is 145. It is to be noted that the fixation of the Daunorubicin on the polymer by the intermediate of a peptide reduces principally its secondary toxicity, which permits the use of significant dosage in equivalent of Daunorubicin.

What is claimed is:

1. A macromolecular prodrug having the formula $$M—(P—D)_n \quad (I)$$

Wherein M is the residue of a polymeric molecule wherein at least 20% of the units of the polymer are polyhydroxylated, M being selected from the group consisting of (1) the residue of a polymer IA having units of the formula:

$$—CH(R')—C(R^2)(X^1)— \quad \text{and} \quad —CH(R^1)—C(R^2)(X^2)—$$
$$(II\ A) \hspace{4em} (III\ A)$$

Wherein
$R^1$ and $R^2$ represent hydrogen or lower alkyl,
$X^1$ represents —Co—NH—$R^3$
$X^2$ represents —CO—NH—X—CO—P—D,
$R^3$ represents a polyhydroxylated hydrocarbon and
X represents a hydrocarbon group having 1–8 carbon atoms, optionally interrupted by at least one oxygen, sulfur or nitrogen heteroatom, (2) the residue of a polymer IB having units of the formulas:

$$—CO—CH(X^3)—NH— \quad \text{and} \quad —CO—CH(X^4)—NH—$$
$$(II\ B) \hspace{5em} (III\ B)$$

wherein
$X^3$ represents —(CH_2)_x—NH—CO—$R^4$,
$x^4$ represents —(CH_2)_x—NH—CO—P—D,
x is a number ranging from 1 to 4,
$R^4$ is a polyhydroxylated hydrocarbon, and (3) the residue of a polymer IC having units of the formulas:

$$—CO—CH(X^5)—NH— \quad \text{and} \quad —CO—CH(X^6)—NH—$$
$$(II\ C) \hspace{5em} (III\ C)$$

wherein
$X^5$ represents —(CH_2)_y—CO—NH—$R^5$,
$X^6$ represents —(CH_2)_y—CO—P—D,
y is a whole number ranging from 1 to 4,
$R^5$ is a polyhydroxylated hydrocarbon, P is a peptidyl group including a sequence which is hydrolyzable by a protease,
D is the residue of a drug molecule and
n represents the number of drug molecules D fixed to the polymeric molecule M.

2. The prodrug of claim 1 wherein the ratio of the average number of molecules of said drug or active substance fixed on one molecule of polymer to the average number of hydroxyl groups present on one molecule of polymer ranges from $10^{-2}$ to $10^{-4}$.

3. The prodrug of claim 1 wherein said drug is an amino drug linked to the peptidyl group P by its C-terminal extremity and in which the peptidyl group is linked to the polymeric molecule by the intermediary of a covalent bond.

4. The prodrug of claim 3 wherein the said covalent bond between the molecule M and the peptide P is an amide bond.

5. The prodrug of claim 1 wherein (P—D) is selected from the group consisting of
(1) -L-Ala-L-Ala-L-Pro-L-Ala-D,
(2) -L-Ala-L-Ala-L-Pro-L-Ala-L-Leu-D,
(3) -L-Ala-L-Ala-L-Pro-L-Ala-D,
(4) -L-Ala-L-Ala-L-Pro-L-Ala-L-Leu-D,
(5) -L-Ala-L-Ala-L-Pro-L-Val-D,
(6) -L-Ala-L-Ala-L-Pro-L-Val-L-Leu-D,
(7) -L-Ala-L-Ala-L-Pro-L-Val-D,
(8) -L-Ala-L-Ala-L-Pro-L-Val-L-Leu-D,
(9) -L-Phe-L-Val-L-Arg-D,
(10) -L-Phe-L-Val-L-Arg-L-Leu-D,
(11) -L-Phe-L-Val-L-Arg-D,
(12) -L-Phe-L-Val-L-Arg-L-Leu-D,
(13) -L-Phe-L-Ala-L-Lys-D,
(14) -L-Phe-L-Ala-L-Lys-L-Leu-D,
(15) -L-Phe-L-Ala-L-Lys-D,
(16) -L-Phe-L-Ala-L-Lys-L-Leu-D,
(17) -Gly-Gly-L-Arg-D,
(18) -Gly-Gly-L-Arg-L-Leu-D,
(19) -Gly-Gly-L-Arg-D,
(20) -Gly-Gly-L-Arg-L-Leu-D,
(21) -Gly-Gly-L-Tyr-D,
(22) -Gly-Gly-L-Tyr-L-Leu-D,
(23) -Gly-Gly-L-Tyr-D,
(24) -Gly-L-Phe-L-Ala-L-Leu-D,
(25) -Gly-L-Pro-L-Arg-L-Leu-D,
(26) -L-Pro-L-Phe-L-Arg-D,
(27) -L-Pro-L-Phe-L-Arg-L-Leu-D,
(28) -L-Pro-L-Phe-L-Arg-D,
(29) -L-Pro-L-Phe-L-Arg-L-Leu-D and
(30) -L-Val-L-Leu-Gy-L-Arg-D.

6. The prodrug of claim 5 wherein each of the (P—D) sequences also contains 1–3 other amino acids between the polymeric molecule and the indicated P sequence.

7. The prodrug of claim 1 wherein said drug D is an antitumor, antibacterial or antiparasite drug.

8. The prodrug of claim 7 wherein said drug is daunorubicin, adriamycin, puromycin, primaquin or chlorquin.

9. A medicine comprising as the active component the prodrug of claim 1.

* * * * *